US008609082B2

(12) United States Patent
Ben-David et al.

(10) Patent No.: US 8,609,082 B2
(45) Date of Patent: Dec. 17, 2013

(54) ADMINISTERING BONE MARROW PROGENITOR CELLS OR MYOBLASTS FOLLOWED BY APPLICATION OF AN ELECTRICAL CURRENT FOR CARDIAC REPAIR, INCREASING BLOOD SUPPLY OR ENHANCING ANGIOGENESIS

(75) Inventors: Tamir Ben-David, Tel Aviv (IL); Omry Ben-Ezra, Jerusalem (IL); Ehud Cohen, Ganei Tikva (IL)

(73) Assignee: Bio Control Medical Ltd., Jerusalem (IL)

( * ) Notice: Subject to any disclaimer, the term of this patent is extended or adjusted under 35 U.S.C. 154(b) by 1592 days.

(21) Appl. No.: 11/340,156

(22) Filed: Jan. 25, 2006

(65) Prior Publication Data

US 2006/0167501 A1    Jul. 27, 2006

Related U.S. Application Data

(60) Provisional application No. 60/646,958, filed on Jan. 25, 2005.

(51) Int. Cl.
*A61N 1/32* (2006.01)
*A61N 1/36* (2006.01)
*A61N 1/362* (2006.01)
*A01N 63/00* (2006.01)

(52) U.S. Cl.
USPC ............................................. 424/93.1; 607/3

(58) Field of Classification Search
None
See application file for complete search history.

(56) References Cited

U.S. PATENT DOCUMENTS

| 3,411,507 | A | 11/1968 | Wingrove |
| 4,019,518 | A | 4/1977 | Maurer et al. |
| 4,161,952 | A | 7/1979 | Kinney et al. |
| 4,338,945 | A | 7/1982 | Kosugi et al. |
| 4,392,496 | A | 7/1983 | Stanton |
| 4,535,785 | A | 8/1985 | van den Honert et al. |
| 4,559,948 | A | 12/1985 | Liss et al. |
| 4,573,481 | A | 3/1986 | Bullara |
| 4,585,005 | A | 4/1986 | Lue et al. |
| 4,602,624 | A | 7/1986 | Naples et al. |
| 4,608,985 | A | 9/1986 | Crish et al. |
| 4,628,942 | A | 12/1986 | Sweeney et al. |
| 4,632,116 | A | 12/1986 | Rosen et al. |
| 4,649,936 | A | 3/1987 | Ungar et al. |
| 4,663,102 | A | 5/1987 | Brenman et al. |
| 4,702,254 | A | 10/1987 | Zabara |
| 4,739,764 | A | 4/1988 | Lue et al. |
| 4,867,164 | A | 9/1989 | Zabara |
| 4,926,865 | A | 5/1990 | Oman |
| 4,962,751 | A | 10/1990 | Krauter |
| 5,025,807 | A | 6/1991 | Zabara |
| 5,042,497 | A | 8/1991 | Shapland |
| 5,069,680 | A | 12/1991 | Grandjean |
| 5,170,802 | A | 12/1992 | Mehra |
| 5,178,161 | A | 1/1993 | Kovacs |
| 5,188,104 | A | 2/1993 | Wernicke et al. |
| 5,199,428 | A | 4/1993 | Obel et al. |
| 5,199,430 | A | 4/1993 | Fang et al. |
| 5,203,326 | A | 4/1993 | Collins |
| 5,205,285 | A | 4/1993 | Baker, Jr. |
| 5,215,086 | A | 6/1993 | Terry, Jr. et al. |
| 5,224,491 | A | 7/1993 | Mehra |
| 5,243,980 | A | 9/1993 | Mehra |
| 5,251,621 | A * | 10/1993 | Collins ............................ 607/4 |
| 5,263,480 | A | 11/1993 | Wernicke et al. |
| 5,282,468 | A | 2/1994 | Klepinski |
| 5,292,344 | A | 3/1994 | Douglas |
| 5,299,569 | A | 4/1994 | Wernicke et al. |
| 5,314,495 | A | 5/1994 | Kovacs |
| 5,330,507 | A | 7/1994 | Schwartz |
| 5,334,221 | A | 8/1994 | Bardy |
| 5,335,657 | A | 8/1994 | Terry, Jr. et al. |
| 5,356,425 | A | 10/1994 | Bardy et al. |
| 5,411,531 | A | 5/1995 | Hill et al. |
| 5,423,872 | A | 6/1995 | Cigaina |
| 5,437,285 | A | 8/1995 | Verrier et al. |
| 5,439,938 | A | 8/1995 | Snyder et al. |
| 5,454,840 | A | 10/1995 | Krakovsky et al. |
| 5,487,756 | A | 1/1996 | Kallesoe et al. |
| 5,507,784 | A | 4/1996 | Hill et al. |
| 5,522,854 | A | 6/1996 | Ideker et al. |
| 5,540,730 | A | 7/1996 | Terry, Jr. et al. |

(Continued)

FOREIGN PATENT DOCUMENTS

| EP | 0688577 | 12/1995 |
| EP | 0831954 | 4/1998 |
| WO | WO 01/10375 | 2/2001 |
| WO | WO 01/10432 | 2/2001 |
| WO | WO 01/26729 | 4/2001 |
| WO | WO 02/085448 | 10/2002 |

OTHER PUBLICATIONS

Asahara et al., 1999, Circ. Res. 85: 221-228.*
Chaudhari et al., 2001, Pediatric Diabetes, 2: 195-202.*
Skale et al. "Inhibition of Premature Ventricular Extrastimuli by Subthreshold Conditioning Stimuli." JACC vol. 6. No. 1 Jul. 1985:133-40.*
Wouter J de Jonge, et al., "Stimulation of the vagus nerve attenuates macrophage activation by activating the Jak2-STAT3 signaling pathway," Nature Immunology 6(8):844-51. (2005).
Kevin J. Tracey, "The inflammatory reflex," Nature 420:853-859 (2002).

(Continued)

*Primary Examiner* — Deborah Crouch
*Assistant Examiner* — Titilayo Moloye
(74) *Attorney, Agent, or Firm* — Sugrue Mion, PLLC

(57) ABSTRACT

A method is provided including selecting a patient suffering from a condition, administering cells to the patient selected from the group consisting of: progenitor cells and genetically-modified cells, applying an electrical current to a site of the patient in a vicinity of nervous tissue, and configuring the current to stimulate the nervous tissue. Other embodiments are also described.

18 Claims, 1 Drawing Sheet

(56) References Cited

U.S. PATENT DOCUMENTS

| | | |
|---|---|---|
| 5,540,734 A | 7/1996 | Zabara |
| 5,571,150 A | 11/1996 | Wernicke et al. |
| 5,578,061 A | 11/1996 | Stroetmann et al. |
| 5,602,301 A * | 2/1997 | Field .............................. 800/8 |
| 5,634,462 A | 6/1997 | Tyler et al. |
| 5,645,570 A | 7/1997 | Corbucci |
| 5,658,318 A | 8/1997 | Stroetmann et al. |
| 5,690,681 A | 11/1997 | Geddes et al. |
| 5,690,691 A | 11/1997 | Chen et al. |
| 5,700,282 A | 12/1997 | Zabara |
| 5,707,400 A | 1/1998 | Terry, Jr. et al. |
| 5,711,316 A | 1/1998 | Elsberry et al. |
| 5,716,385 A | 2/1998 | Mittal et al. |
| 5,755,750 A | 5/1998 | Petruska et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 6,006,134 A | 12/1999 | Hill et al. |
| 6,026,326 A | 2/2000 | Bardy |
| 6,058,331 A | 5/2000 | King |
| 6,066,163 A | 5/2000 | John |
| 6,073,048 A | 6/2000 | Kieval et al. |
| 6,086,525 A | 7/2000 | Davey et al. |
| 6,091,977 A | 7/2000 | Tarjan et al. |
| 6,091,992 A | 7/2000 | Bourgeois et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| H1905 H | 10/2000 | Hill |
| 6,134,470 A | 10/2000 | Hartlaub |
| 6,135,978 A * | 10/2000 | Houben et al. .................. 604/66 |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 * | 7/2001 | Hill et al. .......................... 607/9 |
| 6,272,377 B1 | 8/2001 | Sweeney et al. |
| 6,292,695 B1 | 9/2001 | Webster, Jr. et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,511,500 B1 | 1/2003 | Rahme |
| 6,542,774 B2 | 4/2003 | Hill et al. |
| 6,564,096 B2 | 5/2003 | Mest |
| 6,587,727 B2 | 7/2003 | Osorio et al. |
| 6,600,956 B2 | 7/2003 | Maschino et al. |
| 6,610,713 B2 | 8/2003 | Tracey |
| 6,622,041 B2 | 9/2003 | Terry, Jr. et al. |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen et al. |
| RE38,705 E | 2/2005 | Hill et al. |
| 6,865,416 B2 | 3/2005 | Dev et al. |
| 6,895,280 B2 | 5/2005 | Meadows et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,403,819 B1 | 7/2008 | Shelchuk et al. |
| 7,548,780 B2 | 6/2009 | Libbus et al. |
| 2002/0035335 A1 | 3/2002 | Schauerte |
| 2002/0107553 A1 | 8/2002 | Hill et al. |
| 2002/0120304 A1 | 8/2002 | Mest |
| 2003/0018367 A1 | 1/2003 | DiLorenzo |
| 2003/0040774 A1 | 2/2003 | Terry, Jr. et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0100924 A1 | 5/2003 | Foreman et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236558 A1 | 12/2003 | Whitehurst et al. |
| 2004/0002740 A1 * | 1/2004 | Lee ................................. 607/9 |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0215289 A1 | 10/2004 | Fukui |
| 2004/0243182 A1 | 12/2004 | Cohen et al. |
| 2004/0249416 A1 | 12/2004 | Yun et al. |
| 2005/0119704 A1 * | 6/2005 | Peters et al. ...................... 607/3 |
| 2005/0131467 A1 | 6/2005 | Boveja |
| 2005/0187584 A1 | 8/2005 | Denker et al. |
| 2005/0222644 A1 | 10/2005 | Killian et al. |
| 2006/0015153 A1 | 1/2006 | Gliner et al. |
| 2006/0047213 A1 * | 3/2006 | Gavriely et al. .............. 600/513 |
| 2006/0052831 A1 | 3/2006 | Fukui |
| 2006/0074450 A1 | 4/2006 | Boveja et al. |
| 2006/0129205 A1 | 6/2006 | Boveja et al. |
| 2007/0027487 A1 | 2/2007 | Mika et al. |

OTHER PUBLICATIONS

J. Edwin Blalock, "Harnessing a Neural-immune Circuit to Control Inflammation and Shock," *J. Exp. Med.* © The Rockefeller University Press 195(6):F25-F28 (2002).

Kudo, M. et al., (2003) "Implantation of bone marrow stem cells reduces the infarction and fibrosis in ischemic mouse heart," *Journal of Molecular and Cellular Cardiology* 35:1113-1119.

Li, D. et al., (1999) "Promotion of Atrial Fibrillation by Heart Failure in Dogs: Atrial Remodeling of a Different Sort," *Circulation* 100(1):87-95.

Perin, E. and Silva, G., (2004) "Stem cell therapy for cardiac diseases," *Current Opinion Hematology* 11:399-403.

Tang, Y. et al., (2004) "Autologous mesenchymal stem cell transplantation induce VEGF and neovascularization in ischemic myocardium," *Regulatory Peptides* 117:3-10.

Vanoli, E. et al., (1991) "Vagal stimulation and prevention of sudden death in conscious dogs with a healed myocardial infarction," *Circulation Research* 68(5):1471-1481.

Wang, H. et al., (2003) "Nicotinic acetylcholine receptor alpha-7 subunit is an essential regulator of inflammation," *Nature* 421:384-388.

Bernik, T. et al., (2002) "Pharmacological stimulation of the cholinergic antiinflammatory pathway," *Journal of Experimental Medicine* 195(6):781-788.

Borovikova, L. et al., (May 25, 2000) "Vagus nerve stimulation attenuates the systemic inflammatory response to endotoxin," *Nature* 405:458-462.

De Ferrari, G. et al, (1991) "Vagal reflexes and survival during acute myocardial ischemia in conscious dogs with healed myocardial infarction," *American Journal of Physiology* 261(1 Pt 2):H63-H69.

Duan, H. et al., (2003) "Treatment of myocardial ischemia with bone marrow-derived mesenchymal cells overexpressing hepatocyte growth factor," *Molecular Therapy* 8(3):467-474.

(56) References Cited

OTHER PUBLICATIONS

Feliciano, L. and Henning, R., (1998) "Vagal nerve stimulation releases vasoactive intestinal peptide which significantly increases coronary artery blood flow," *Cardiovascular Research* 40:45-55 (Exhibit 5).

Kinnaird, T. et al., (2004) "Local delivery of marrow-derived stromal cells augments collateral perfusion through paracrine mechanisms," *Circulation* 109:1543-1550.

Kinnaird, T. et al., (2004) "Marrow-derived stromal cells express genes encoding a broad spectrum of arteriogenic cytokines and promote in vitro and in vivo arteriogenesis through paracrine mechanisms," *Circulation Research* 94:678-685.

S. Bibevski, et al., "Ganglionic mechanisms contribute to diminished vagal control in heart failure," Circulation 99:2958-2963 (1999).

A.M. Bilgutay, et al., "Vagal tuning: A new concept in the treatment of supraventricular arrhythmias, angina pectoris, and heart failure," *J. Thoracic Cardiovasc. Surg.* 56(1): 71-82 (1968).

K.M. Bluemel, et al., "Parasympathetic postganglionic pathways to the sinoatrial node," Am.J.Physiol. 259 (Heart Circ.Physiol. 28):H1504-1510 (1990).

M.D.Carlson, et al., "Selective stimulation of parasympathetic nerve fibers to the human sinoatrial node," Circulation 85:1311-1317 (1992).

Shih-Ann Chen, et al., "Intracardiac stimulation of human parasympathetic nerve fibers induces negative dromotropic effects: implication with the lesions of radiofrequency catheter ablation," *J. Cardiovasc. Electrophysiol.* 9(3):245-252 (1998).

T.B. Cooper, et al., "Neural effects on sinus rate and atrioventricular conduction produced by electrical stimulation from a transvenous electrode catheter in the canine right pulmonary artery," *Circ. Res.* 46(I):48-57 (1980).

J.E. Cummings, et al., "Preservation of the anterior fat pad paradoxically decreases the incidence of postoperative atrial fibrillation in humans," *J. Am. Coll. Cardiol.* 43(6):994-1000 (2004).

G.S. Friedrichs, "Experimental models of atrial fibrillation/flutter," J.Pharmacol. & Toxicol. Methods 43:117-123 (2000).

V. Fuster, et al., "ACC/AHA/ESC guidelines for the management of patients with atrial fibrillation," J.Am.Coll.Cardiol. 38(4):1266i-lxx (2001).

S. Garrigue, et al., "Post-ganglionic vagal stimulation of the atrioventricular node reduces ventricular rate during atrial fibrillation," PACE 21(4) Part II:878 (1998).

J.J. Goldberger, et al., "New technique for vagal nerve stimulation," J.Neurosci.Methods 91:109-114 (1999).

A. Hjalmarson, "Prevention of sudden cardiac death with beta blockers," Clin.Cardiol. 22 (Suppl. V): V-II-V-15 (1999).

L. Jideus, "Atrial fibrillation after coronary artery bypass surgery," *Acta Universitatis; Upsaliensis*: Comprehensive Summaries of Uppsala Dissertations from the Faculty of Medicine 1093:1-56 (2001).

H. Kwan, et al., "Cardiovascular adverse drug reactions during initiation of antiarrhythmic therapy for atrial fibrillation," Can.J.Hosp. Pharm. 54:10-14 (2001).

D. Li, et al., "Promotion of atrial fibrillation by heart failure in dogs," Circulation 100:87-95 (1999).

M. Manfredi, "Differential block of conduction of larger fibers in peripheral nerve by direct current," Arch.ltal.Biol. 108:52-71 (1970).

T.N. Mazgalev, "AV nodal physiology," Heart Rhythm Society (www.hrsonline.org), no date.

P.L. Pagé, et al., "Regional distribution of atrial electrical changes induced by stimulation of extracardiac and intracardiac neural elements," *J. Thorac. Cardiovasc. Surg.* 109:377-88 (1995).

N.J.M. Rijkhoff, et al., "Selective stimulation of small diameter nerve fibers in a mixed bundle," *Proceedings of the Annual Project Meeting Sensations/Neuros and Mid Term Review Meeting Neuros*, Apr. 21-23, 1999:20-21 (1999).

M.S. Waninger, et al., "Electrophysiological control of ventricular rate during atrial fibrillation," PACE 23:1239-1244 (2000).

Y. Zhang, et al., "Optimal ventricular rate slowing during atrial fibrillation by feedback AV nodal-selective vagal stimulation", *Am. J. Physiol. Head Circ. Physiol.* 282:H1102-H1110 (2002).

Y. Furukawa, et al., "Differential blocking effects of atropine and gallamine on negative chronotropic and dromotropic responses to vagus stimulation in aneshthetized dogs," *J. Pharmacol. & Exper. Therapeut.* 251(3):797-802 (1989).

Office Action, issued Feb. 5, 2010, in connection with U.S. Appl. No. 11/974,951, filed Oct. 16, 2007.

Office Action, issued Feb. 24, 2010, in connection with U.S. Appl. No. 10/866,601, filed Jun. 10, 2004.

Office Action, issued Feb. 24, 2010, in connection with U.S. Appl. No. 11/359,266, filed Feb. 21, 2006.

Office Action, issued Jun. 30, 2010, in connection with U.S. Appl. No. 11/977,923, filed Oct. 25, 2007.

\* cited by examiner

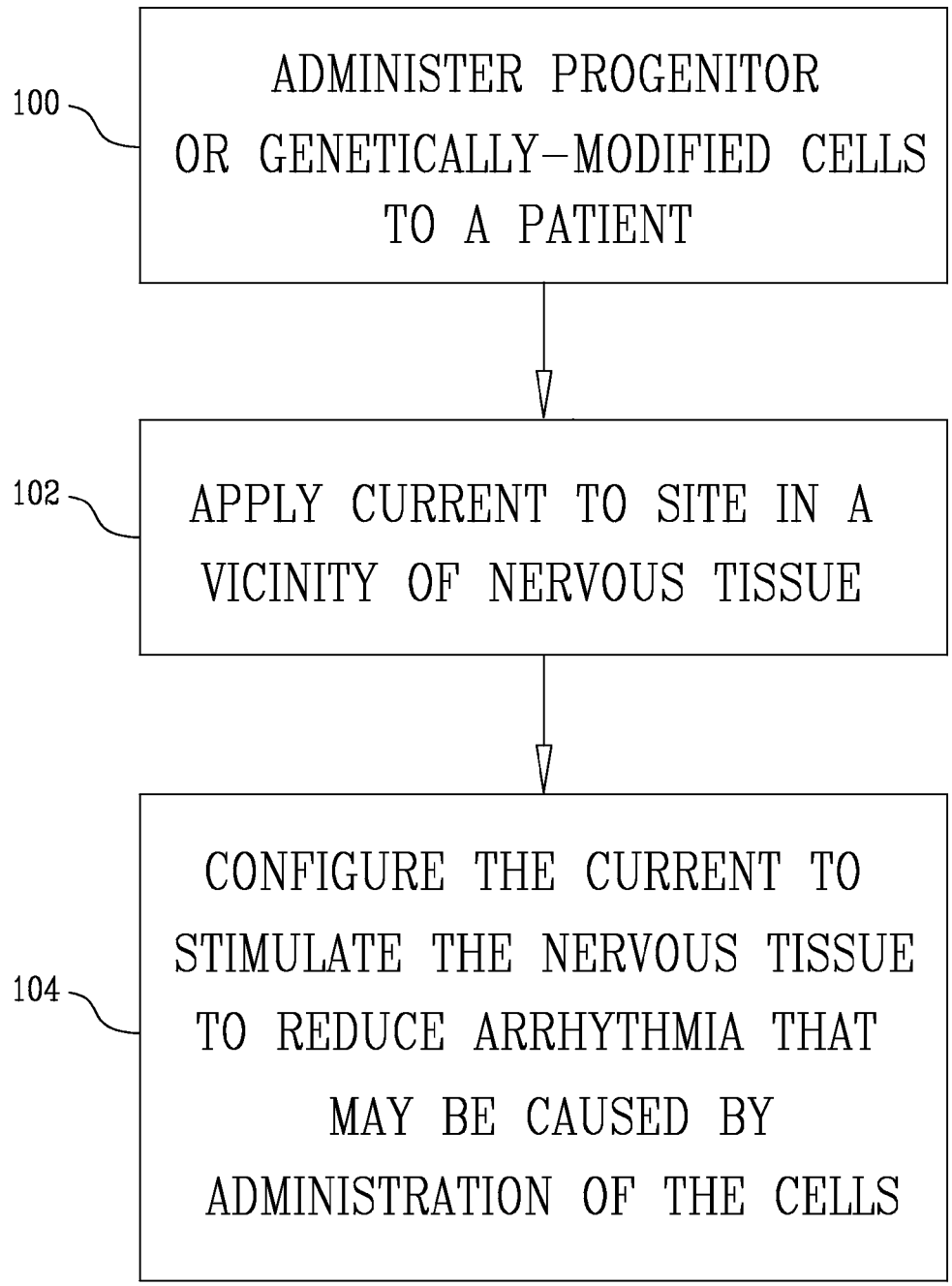

ADMINISTERING BONE MARROW PROGENITOR CELLS OR MYOBLASTS FOLLOWED BY APPLICATION OF AN ELECTRICAL CURRENT FOR CARDIAC REPAIR, INCREASING BLOOD SUPPLY OR ENHANCING ANGIOGENESIS

CROSS-REFERENCES TO RELATED APPLICATIONS

The present patent application claims the benefit of U.S. Provisional Patent Application 60/646,958, filed Jan. 25, 2005, entitled, "Method to enhance progenitor cells or genetically-modified cells therapy," which is assigned to the assignee of the present application and is incorporated herein by reference.

FIELD OF THE INVENTION

The present invention relates generally to cell therapy, and specifically to methods for enhancing progenitor or genetically-modified cell therapy.

BACKGROUND OF THE INVENTION

Cellular therapy is an emerging field of medicine that uses cells that evolve from transplanted progenitor cells or genetically-modified cells to repair damaged tissue and diseased organs, or to generate new tissues with desired functions. Stem cell therapy presents a way to treat many degenerative diseases caused by death or malfunction of specific body tissues by replacing or restoring the damaged tissue cells.

Cellular therapy is currently used to treat leukemia by transplanting bone marrow that contains blood progenitor cells or genetically-modified cells which differentiate into new, cancer-free blood cells. Body organs that may potentially be treated using progenitor or genetically-modified cell therapy include body muscles and bones, nerves, skin, blood cells, the heart, the brain, the liver, the pancreas, and the spinal cord. Conditions that may be treated using such cell therapy include leukemia, sickle cell anemia, spinal cord injury, heart disease, Parkinson's disease, Alzheimer's disease, burns, cirrhosis, hepatitis, muscular dystrophy, diabetes, arthritis, and osteoporosis-related injuries.

Bone marrow progenitor or genetically-modified cell therapy for cardiac repair has been tested in animal models and has shown some evidence of increased neovascularization (with reduced myocardial ischemia) and consequent improvement in cardiac function (Tang Y L et al., Duan H F et al., and Kudo M et al., cited hereinbelow). It has also been shown that bone marrow progenitor cells or genetically-modified cells may directly contribute to an increase in contractility, and may limit infarct expansion and remodeling. One of the obstacles for successful engraftment of the stem cells is insufficient blood supply and angiogenesis. The use of growth factors to promote arteriogenesis and vasculogenesis, which may result in cardiac repair, has been evaluated (e.g., see the two articles cited hereinbelow by Kinnaird T et al.).

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

US Patent Application Publication 2004/0158290 to Girouard et al., which is incorporated herein by reference, describes a method for cell and electrical therapy of living tissue including administration of exogenous cells into a region of injured tissue and application of electrical energy. In one application, the combined cell and electrical therapy is applied in vivo to damaged heart tissue. Minimally-invasive procedures are used to apply the cell therapy, and the electrical therapy is provided via an implantable pulse generator. In one application, an implantable pacemaker is used in the VDD mode with an atrioventricular delay kept relatively short when compared to the intrinsic atrioventricular delay.

US Patent Application Publication 2005/0288721 to Girouard et al., which is incorpoated herein by reference, describes a system that delivers cardiac pacing therapy and chemical and/or biological therapy to modulate myocardial tissue growth in a heart after myocardial infarction (MI). The system includes an agent delivery device to release one or more agents to an MI region to modulate myocardial tissue growth in that region, and a cardiac rhythm management (CRM) device to deliver pacing pulses to enhance the effects of the one or more agents by altering myocardial wall stress and cardiac workload. In an embodiment, the agent includes a vector, which may include a coding sequence of interest for gene therapy. For some applications, the agent enhances localization, implantation, or proliferation of stem cells at the cardiac region. For some applications, cellular engraftment, cellular proliferation, cellular differentiation, cellular survival, and/or cellular function, e.g., contractile function, of the donor cells in the recipient is further enhanced by the electrical therapy and/or agent administration.

US Patent Application Publication 2005/0192637 to Girouard et al., which is incorporated herein by reference, describes a gene regulatory system that controls gene therapy by emitting one or more forms of energy that regulate gene expression by triggering promoters. The system includes a sensor to sense a signal indicative of a need for the gene therapy as well as responses to the gene therapy. The regulation of the gene expression is controlled based on the sensed signal and/or a user command. In an embodiment, the system delivers one or more electrical therapies in conjunction with the gene therapy.

US Patent Application Publication 2006/0015146 to Girouard et al., which is incorporated herein by reference, describes an implantable system which includes a gene/protein delivery device and a pulse generator, as well as a method for preparing the gene/protein delivery device and using the system. In an embodiment, the implantable system detects a predetermined condition or event and, in response, delivers gene(s) and/or protein(s) in conjunction with delivering pacing and/or defibrillation pulses.

U.S. Pat. No. 6,348,444 to Chappel, which is incorporated herein by reference, describes techniques for the use of human growth hormone for the manufacture of a medicament for stimulating hematopoiesis and immune reconstitution to be administered to a patient in need thereof about 30 days post-transplantation of hematopoietic stem cells.

US Patent Application Publication 2004/0247574 to Christopherson et al., which is incorporated herein by reference, describes techniques for improving engraftment efficiency in stem cell transplants by improving stem cell homing to bone marrow.

U.S. Pat. No. 6,383,481 to Ikehara et al., which is incorporated herein by reference, describes techniques for transplanting hemopoietic stem cells, which comprise subjecting a recipient to a radiation treatment using an effective exposure dose for hemopoietic stem cell transplantation in advance and administering hemopoietic stem cells from a donor from the portal vein.

US Patent Application Publication 2002/0182186 to Loeb, which is incorporated herein by reference, describes techniques for use with stem cells, bone marrow, or bone marrow enriched with stem cell compositions suitable for tissue repair.

The following articles, all of which are incorporated herein by reference, may be of interest:

Perin E C et al., "Stem cell therapy for cardiac diseases," Curr Opin Hematol 11(6):399-403 (2004)

Tang Y L et al., "Autologous mesenchymal stem cell transplantation induce [sic] VEGF and neovascularization in ischemic myocardium," Regul Pept 117:3-10 (2004)

Duan H F et al., "Treatment of myocardial ischemia with bone marrow-derived mesenchymal progenitor cells or genetically-modified cells overexpressing hepatocyte growth factor," Mol Ther 3:467-474 (2003)

Kudo M et al., "Implantation of bone marrow progenitor cells or genetically-modified cells reduces the infarction and fibrosis in ischemic mouse heart," J Mol Cell Cardiol 35:1113-1119 (2003)

Kinnaird T et al., "Local delivery of marrow-derived stromal cells augments collateral perfusion through paracrine mechanisms," Circulation 109:1543-1549 (2004)

Kinnaird T et al., "Marrow-derived stromal cells express genes encoding a broad spectrum of arteriogenic cytokines and promote in vitro and in vivo arteriogenesis through paracrine mechanisms," Circ Res 94:678-685 (2004)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Tracey K J, "The inflammatory reflex," Nature Vol 420 19/26 December 2002

Bernik T R, "Pharmacological Stimulation of the Cholinergic Antiinflammatory Pathway," J. Exp. Med. Volume 195, Number 6, Mar. 18, 2002 781-788

Blalock J E, "Harnessing a Neural-immune Circuit to Control Inflammation and Shock," J. Exp. Med. Volume 195, Number 6, Mar. 18, 2002 F25-F28

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 6,610,713 to Tracey, which is incorporated herein by reference, describes apparatus for inhibiting inflammatory cytokine production, for treating a condition mediated by the cytokine cascade such as allergy, asthma, sepsis, septic abortion or urethritis. The apparatus uses cholinergic agonist and vagus nerve stimulation.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

SUMMARY OF THE INVENTION

In some embodiments of the present invention, a method for enhancing progenitor or genetically-modified cell therapy comprises administering progenitor or genetically-modified cells to a patient, applying a current to a site of the patient in a vicinity of nervous tissue, and configuring the current to stimulate the nervous tissue. For some applications, the nervous tissue includes parasympathetic nervous tissue, and the current is configured to cause parasympathetic activation of the nervous tissue. For some applications, the current is applied to a portion of a vagus nerve of the patient that innervates the heart. Alternatively, the current is applied to another portion of the vagus nerve, an epicardial fat pad, a carotid artery, a coronary body, a coronary sinus, a vena cava vein, or an internal jugular vein. The current is applied prior to, during, and/or following administration of the progenitor or genetically-modified cells.

Such stimulation generally improves the engraftment of the progenitor or genetically-modified cells, improves survival of the cells, and enhances the function of the cells within the target tissue. For example, such parasympathetic stimulation may enhance the contractility and survival of progenitor cells implanted in the myocardium.

The methods described herein are suitable for treatment of conditions such as leukemia, sickle cell anemia, spinal cord injury, heart disease, Parkinson's disease, Alzheimer's disease, burns, cirrhosis, hepatitis, muscular dystrophy, diabetes, arthritis, and osteoporosis-related injuries.

There is therefore provided, in accordance with an embodiment of the present invention, a method including:

selecting a patient suffering from a condition;

administering cells to the patient selected from the group consisting of: progenitor cells and genetically-modified cells;

applying an electrical current to a site of the patient in a vicinity of nervous tissue; and configuring the current to stimulate the nervous tissue.

Typically, applying the current includes configuring the current to enhance a parameter selected from the group consisting of: a measure of functionality of the cells, an extent to which the cells are directed towards a target tissue, and a level of integration of the cells with a target tissue. For example, the parameter may include the measure of functionality of the cells, and configuring the current to enhance the parameter may include configuring the current to decrease a rate of mortality of the cells.

In an embodiment, the site includes a non-cardiac site of the patient, and applying the current includes applying the current to the non-cardiac site. For some applications, applying the current does not include configuring the current to pace a heart of the patient.

In an embodiment, configuring the current to stimulate the nervous tissue includes configuring the current to have an amplitude less than a cardiac pacing threshold of the patient.

In an embodiment, configuring the current to stimulate the nervous tissue includes setting the current to have an amplitude between 1 and 20 mA, and a frequency between 0.01 and 10 Hz.

In an embodiment, applying the current includes applying the current during a refractory period of a heart of the patient.

For some applications, applying the current includes configuring the current to enhance capillary growth at a cardiac site of: the patient. Alternatively or additionally, applying the current includes configuring the current to reduce arrhythmia that may be caused by administration of the cells.

In an embodiment, the nervous tissue includes parasympathetic nervous tissue, and configuring the current includes configuring the current to stimulate the parasympathetic nervous tissue. For some applications, the site is selected from the group consisting of: a vagus nerve, an epicardial fat pad, a carotid artery, a coronary body, a coronary sinus, a vena cava vein, and an internal jugular vein, and applying the current to the site includes applying the current to the selected site. For example, the site may include the vagus nerve, and applying the current may include applying the current to the vagus nerve.

For some applications, administering the cells includes administering cells capable of differentiating into contractile units after administration. For example, the cells may be selected from the group consisting of: skeletal myoblasts, and smooth muscle myoblasts, and administering the cells may include administering the selected myoblasts.

For some applications, administering the cells includes administering cells capable of differentiating into endothelial cells after administration. For example, the cells may be selected from the group consisting of: bone marrow progenitor cells, and genetically-modified cells, and administering the cells may include administering the selected cells.

For some applications, applying the current includes configuring the current to reduce inflammation at a cardiac site of the patient. For example, configuring the current to reduce inflammation may include configuring the current to reduce inflammation to reduce a complication that might result from administration of the cells.

In an embodiment, the condition includes neither myocardial infarct nor heart failure, and selecting the patient includes selecting the patient suffering from neither myocardial infarct nor heart failure.

In an embodiment, the condition includes a condition selected from the group consisting of: myocardial infarct, and heart failure, and selecting the patient includes selecting the patient suffering from the selected condition.

For some applications, administering the cells includes selecting cells capable of promoting: function of a heart of the patient, function of a liver of the patient, function of a kidney of the patient, function of bone marrow of the patient, function of skin of the patient, function of a digestive system of the patient, function of an immune system of the patient, function of neural tissue of the patient, function of blood vessels of the patient, production of blood cells of the patient, or growth of hair of the patient.

For some applications, applying the current includes applying the current after and not before administering the cells.

Alternatively, applying the current includes initiating application of the current before administering the cells. For some applications, initiating application of the current includes initiating application of the current at least one day prior to administering the cells. For some applications, applying the current includes applying the current before and after administering the cells. For some applications, applying the current includes applying the current before and not after administering the cells.

In an embodiment, applying the current includes: placing a set of one or more electrodes within a body of the patient; driving the set of electrodes to apply the current; and removing the set of electrodes from the body within 8 weeks following placing the set of electrodes within the body.

In an embodiment, applying the current includes: placing a set of one or more electrodes within a body of the patient; driving the set of electrodes to apply the current; and leaving the set of electrodes in the body for more than 8 weeks following placing the set of electrodes within the body. For some applications, applying the current includes applying the current only within 8 weeks of a time of administering the cells. For some applications, applying the current includes applying the current only within 48 hours of a time of administering the cells. For some applications, applying the current includes applying the current for at least one hour before administering the cells, and for at least three hours following administering the cells.

In an embodiment, applying the current includes assessing, prior to administering the cells, a response of the patient to the application of the current, and modifying an administration parameter of the administration of the cells in response to the assessment. For some applications, the administration parameter is selected from the group consisting of: a route of the administration of the cells, a type of the cells, and an amount of the cells, and modifying the administration parameter includes modifying the selected administration parameter in response to the assessment. For some applications, modifying the administration parameter includes modifying a number of the cells administered in response to the assessment. For some applications, modifying the administration parameter includes modifying a time of administration of the cells in response to the assessment. Alternatively or additionally, modifying the administration parameter includes modifying a ratio of types of cells administered, in response to the assessment.

For some applications, assessing the response includes performing an action selected from the group consisting of: imaging a target treatment site of the patient, assessing blood flow to a target treatment site of the patient, and performing biochemical analysis of gene expression in a target treatment site of the patient.

For some applications, the condition includes a condition selected from the group consisting of: myocardial infarct, and heart failure, and selecting the patient includes selecting the patient suffering from the selected condition.

There is further provided, in accordance with an embodiment of the present invention, a method including:
  selecting a patient suffering from a condition;.
  identifying the patient as being one who would benefit from enhanced migration and differentiation of native, non-administered cells of the patient selected from the group consisting of: progenitor cells of the patient, and cells of the patient having a desired genotype;

applying an electrical current to a site of the patient in a vicinity of nervous tissue; and configuring the current to stimulate the nervous tissue to enhance migration and differentiation of the native, non-administered cells of the patient Typically, applying the current includes configuring the current to enhance a measure of functionality of the cells. For example, configuring the current to enhance the measure of functionality may include configuring the current to decrease a rate of mortality of the cells.

In an embodiment, the site includes a non-cardiac site of the patient, and applying the current includes applying the current to the non-cardiac site. For some applications, applying the current does not include configuring the current to pace a heart of the patient.

In an embodiment, configuring the current to stimulate the nervous tissue includes configuring the current to have an amplitude less than a cardiac pacing threshold of the patient.

In an embodiment, configuring the current to stimulate the nervous tissue includes setting the current to have an amplitude between 1 and 20 mA, and a frequency between 0.01 and 10 Hz.

In an embodiment, applying the current includes applying the current during a refractory period of a heart of the patient.

For some applications, applying the current includes configuring the current to enhance the migration and differentiation of cells capable of differentiating into contractile units after administration. For some applications, the cells are selected from the group consisting of: skeletal myoblasts, and smooth muscle myoblasts, and configuring the current includes configuring the current to enhance the migration and differentiation of the selected myoblasts.

For some applications, applying the current includes configuring the current to enhance the migration and differentiation of cells capable of differentiating into endothelial cells after administration. For some applications, the cells are selected from the group consisting of: bone marrow progenitor cells, and genetically-modified cells, and configuring the current includes configuring the current to enhance the migration and differentiation of the selected cells.

For some applications, applying the current includes configuring the current to enhance capillary growth at a cardiac site of the patient. Alternatively or additionally, applying the current includes configuring the current to reduce arrhythmia that may be caused by administration of the cells.

For some applications, applying the current includes configuring the current to reduce inflammation at a cardiac site of the patient.

In an embodiment, the condition includes neither myocardial infarct nor heart failure, and selecting the patient includes selecting the patient suffering from neither myocardial infarct nor heart failure.

For some applications, applying the current includes configuring the current to enhance the migration and differentiation of cells capable of promoting: function of a heart of the patient, function of a liver of the patient, function of a kidney of the patient, function of bone marrow of the patient, function of skin of the patient, function of a digestive system of the patient, function of an immune system of the patient, function of neural tissue of the patient, function of blood vessels of the patient, production of blood cells of the patient, or growth of hair of the patient.

There is still further provided, in accordance with an embodiment of the present invention, a method including:

selecting a patient suffering from a condition;

administering cells to a systemic blood circulation of the patient, the cells selected from the group consisting of progenitor cells and genetically-modified cells;

applying an electrical current to a current-application site of the patient in a vicinity of nervous tissue; and configuring the current to stimulate the nervous tissue to direct the cells to a target treatment site of the patient.

In an embodiment, the site includes a non-cardiac site of the patient, and applying the current includes applying the current to the non-cardiac site. For some applications, applying the current does not include configuring the current to pace a heart of the patient.

In an embodiment, configuring the current to stimulate the nervous tissue includes configuring the current to have an amplitude less than a cardiac pacing threshold of the patient.

In an embodiment, configuring the current to stimulate the nervous tissue includes setting the current to have an amplitude between 1 and 20 mA, and a frequency between 0.01 and 10 Hz.

In an embodiment, applying the current includes applying the current during a refractory period of a heart of the patient.

In an embodiment, the condition includes neither myocardial infarct nor heart failure, and selecting the patient includes selecting the patient suffering from neither myocardial infarct nor heart failure.

Typically, applying the current includes configuring the current to enhance a measure of functionality of the cells. For example, configuring the current to enhance the measure of functionality may include configuring the current to decrease a rate of mortality of the cells.

In an embodiment, the current-application site is remote from the target treatment site. For some applications, the target treatment site includes a liver of the patient, the current-application site is selected from the group consisting of: a vagus nerve and a branch of the vagus nerve, and applying the current includes applying the current to the selected current-application site. For some applications, the target treatment site includes a heart of the patient, the current-application site is selected from the group consisting of: a vagus nerve and a branch of the vagus nerve, and applying the current includes applying the current to the selected current-application site. For some applications, the target treatment site includes a brain of the patient, the current-application site includes a peripheral nerve of the patient, and applying the current includes applying the current to the peripheral nerve. For some applications, the target treatment site includes a peripheral nerve of the patient, the current-application site is selected from the group consisting of: a spinal cord of the patient, and a brain of the patient, and applying the current includes applying the current to the selected current-application site.

In an embodiment, the target treatment site includes a heart of the patient, the current-application site is selected from the group consisting of: an epicardial fat pad, a carotid artery, a coronary body, a coronary sinus, a vena cava vein, and an internal jugular vein, and applying the current includes applying the current to the selected current-application site.

In an embodiment, the target treatment site includes a brain of the patient, the current-application site is selected from the group consisting of: a cranial nerve, and the brain, and applying the current includes applying the current to the selected current-application site.

In an embodiment, the target treatment site includes a peripheral nerve of the patient, the current-application site includes tissue that is innervated by the nerve, and applying the current includes applying the current to the innervated tissue.

For some applications, administering the cells includes administering cells capable of differentiating into contractile units after administration. For example, the cells may be selected from the group consisting of: skeletal myoblasts, and smooth muscle myoblasts, and administering the cells may include administering the selected myoblasts.

For some applications, administering the cells includes administering cells capable of differentiating into endothelial cells after administration. For example, the cells may be selected from the group consisting of: bone marrow progenitor cells, and genetically-modified cells, and administering the cells may include administering the selected cells.

For some applications, applying the current includes configuring the current to enhance capillary growth at a cardiac site of the patient. Alternatively or additionally, applying the current includes configuring the current to reduce arrhythmia that may be caused by administration of the cells.

For some applications, applying the current includes configuring the current to reduce inflammation at a cardiac site of the patient. For example, configuring the current to reduce inflammation may include configuring the current to reduce inflammation to reduce a complication that might result from administration of the cells.

For some applications, applying the current includes applying the current after and not before administering the cells. Alternatively, applying the current includes initiating application of the current before administering the cells. For some applications, initiating application of the current includes initiating application of the current at least one day prior to administering the cells.

For some applications, applying the current includes applying the current before and after administering the cells. For some applications, applying the current includes applying the current before and not after administering the cells.

In an embodiment, applying the current includes: placing a set of one or more electrodes within a body of the patient; driving the set of electrodes to apply the current; and removing the set of electrodes from the body within 8 weeks following placing the set of electrodes within the body.

In an embodiment, applying the current includes: placing a set of one or more electrodes within a body of the patient; driving the set of electrodes to apply the current; and leaving the set of electrodes in the body for more than 8 weeks following placing the set of electrodes within the body. For some applications, applying the current includes applying the current only within 8 weeks of a time of administering the cells. For some applications, applying the current includes applying the current only within 48 hours of a time of administering the cells. For some applications, applying the current includes applying the current for at least one hour before administering the cells, and for at least three hours following administering the cells.

In an embodiment, applying the current includes assessing, prior to administering the cells, a response of the patient to the application of the current, and modifying an administration parameter of the administration of the cells in response to the assessment. For some applications, the administration parameter is selected from the group consisting of: a route of the administration of the cells, a type of the cells, and an amount of the cells, and modifying the administration parameter includes modifying the selected administration parameter in response to the assessment. For some applications, modifying the administration parameter includes modifying a number of the cells administered in response to the assessment.

For some applications, modifying the administration parameter includes modifying a time of administration of the cells in response to the assessment. Alternatively or additionally, modifying the administration parameter includes modifying a ratio of types of cells administered, in response to the assessment.

For some applications, assessing the response includes performing an action selected from the group consisting of: imaging a target treatment site of the patient, assessing blood flow to a target treatment site of the patient, and performing biochemical analysis of gene expression in a target treatment site of the patient.

There is also provided, in accordance with an embodiment of the invention, a method including:
selecting a patient suffering from a condition;
administering cells to the patient selected from the group consisting of: progenitor cells and genetically-modified cells;
applying an electrical current to a site of the patient in a vicinity of non-cardiac tissue; and
configuring the current to stimulate the non-cardiac tissue.

In an embodiment, applying the current includes configuring the current to enhance a parameter selected from the group consisting of: a measure of functionality of the cells, an extent to which the cells are directed towards a target tissue, and a level of integration of the cells with a target tissue.

In an embodiment, the parameter includes the measure of functionality of the cells, and configuring the current to enhance the parameter includes configuring the current to decrease a rate of mortality of the cells.

In an embodiment, the condition includes a condition selected from the group consisting of: myocardial infarct and heart failure, and selecting the patient includes selecting the patient suffering from the selected condition.

In an embodiment, applying the current does not include configuring the current to pace a heart of the patient.

In an embodiment, configuring the current to stimulate the tissue includes configuring the current to have an amplitude less than a cardiac pacing threshold of the patient.

In an embodiment, configuring the current to stimulate the tissue includes setting the current to have an amplitude between 1 and 20 mA, and a frequency between 0.01 and 10 Hz.

In an embodiment, applying the current includes applying the current during a refractory period of a heart of the patient.

In an embodiment, applying the current includes configuring the current to enhance capillary growth at a cardiac site of the patient.

In an embodiment, applying the current includes configuring the current to reduce arrhythmia that may be caused by administration of the cells.

In an embodiment, administering the cells includes administering cells capable of differentiating into contractile units after administration.

In an embodiment, the cells are selected from the group consisting of: skeletal myoblasts, and smooth muscle myoblasts, and administering the cells includes administering the selected myoblasts.

In an embodiment, administering the cells includes administering cells capable of differentiating into endothelial cells after administration.

In an embodiment, the cells are selected from the group consisting of: bone marrow progenitor cells, and genetically-modified cells, and administering the cells includes administering the selected cells.

In an embodiment, applying the current includes configuring the current to reduce inflammation at a cardiac site of the patient.

In an embodiment, configuring the current to reduce inflammation includes configuring the current to reduce inflammation to reduce a complication that might result from administration of the cells.

In an embodiment, the condition includes neither myocardial infarct nor heart failure, and selecting the patient includes selecting the patient suffering from neither myocardial infarct nor heart failure.

In an embodiment, administering the cells includes selecting cells capable of promoting function of a heart of the patient.

In an embodiment, administering the cells includes selecting cells from the group consisting of: cells capable of promoting function of a liver of the patient, cells capable of promoting function of a kidney of the patient, cells capable of promoting function of bone marrow of the patient, cells capable of promoting function of skin of the patient, cells capable of promoting function of a digestive system of the patient, cells capable of promoting function of an immune system of the patient, cells capable of promoting function of neural tissue of the patient, cells capable of promoting function of blood vessels of the patient, cells capable of promoting production of blood cells of the patient, and cells capable of promoting growth of hair of the patient.

In an embodiment, applying the current includes applying the current after and not before administering the cells.

In an embodiment, applying the current includes initiating application of the current before administering the cells.

In an embodiment, initiating application of the current includes initiating application of the current at least one day prior to administering the cells.

In an embodiment, applying the current includes applying the current before and after administering the cells.

In an embodiment, applying the current includes applying the current before and not after administering the cells.

In an embodiment, applying the current includes:
placing a set of one or more electrodes within a body of the patient;
driving the set of electrodes to apply the current; and
removing the set of electrodes from the body within 8 weeks following placing the set of electrodes within the body.

In an embodiment, applying the current includes:
placing a set of one or more electrodes within a body of the patient;
driving the set of electrodes to apply the current; and
leaving the set of electrodes in the body for more than 8 weeks following placing the set of electrodes within the body.

In an embodiment, applying the current includes applying the current only within 8 weeks of a time of administering the cells.

In an embodiment, applying the current includes applying the current only within 48 hours of a time of administering the cells.

In an embodiment, applying the current includes applying the current for at least one hour before administering the cells, and for at least three hours following administering the cells.

In an embodiment, applying the current includes assessing, prior to administering the cells, a response of the patient to the application of the current, and modifying an administration parameter of the administration of the cells in response to the assessment.

In an embodiment, the administration parameter is selected from the group consisting of: a route of the administration of the cells, a type of the cells, and an amount of the cells, and modifying the administration parameter includes modifying the selected administration parameter in response to the assessment.

In an embodiment, modifying the administration parameter includes modifying a number of the cells administered in response to the assessment.

In an embodiment, modifying the administration parameter includes modifying a time of administration of the cells in response to the assessment.

In an embodiment, modifying the administration parameter includes modifying a ratio of types of cells administered, in response to the assessment.

In an embodiment, assessing the response includes performing an action selected from the group consisting of: imaging a target treatment site of the patient, assessing blood flow to a target treatment site of the patient, and performing biochemical analysis of gene expression in a target treatment site of the patient.

In an embodiment, administering the cells comprises administering the cells to the non-cardiac tissue.

There is additionally provided, in accordance with an embodiment of the invention, a method including:
selecting a patient suffering from a condition;
administering cells to the patient selected from the group consisting of: progenitor cells and genetically-modified cells; and
applying, to tissue at a myocardial site of the patient, an electrical current that does not pace a heart of the patient.

In an embodiment, applying the current includes applying the current during a refractory period of the heart.

In an embodiment, applying the current includes setting an amplitude of the current to be insufficient to pace the heart.

The present invention will be more fully understood from the following detailed description of embodiments thereof, taken together with the drawing, in which:

BRIEF DESCRIPTION OF THE DRAWING

FIG. 1 is a flowchart schematically illustrating a method for enhancing progenitor or genetically-modified cell therapy, in accordance with some embodiments of the present invention.

DETAILED DESCRIPTION OF EMBODIMENTS

Reference is made to FIG. 1, which is a flowchart schematically illustrating a mehtod for enhancing progenitor or genetically-modified cell therapy, in accordance with some embodiments of the present invention. In some embodiments of the present invention, a method for enhancing progenitor or genetically-modified cell therapy comprises administering progenitor or genetically-modified cells to a patient (at an administration step 100), applying a current to a site of the patient in a vicinity of nervous tissue (at a current application step 102), and configuring the current to stimulate the nervous tissue (at a current configuration step 104). Typically, configuring the current comprises configuring the current to enhance a measure of functionality of the cells. For some applications, the nervous tissue includes parasympathetic nervous tissue, and the current is configured to cause parasympathetic activation of the nervous tissue, thereby increasing parasympathetic tone. For some applications, the current is applied to a portion of a vagus nerve of the patient that innervates the heart. Alternatively, the current is applied to another portion of the vagus nerve, an epicardial fat pad, a carotid artery, a coronary body, a coronary sinus, a vena cava vein, or an internal jugular vein. For some applications, the current-application site includes a non-cardiac site of the patient. Depending upon the particular application, the current is applied prior to, during, and/or following administration of the progenitor or genetically-modified cells.

In an embodiment of the present invention, the method for enhancing progenitor or genetically-modified cell therapy is performed using a system for applying nervous tissue stimulation to a patient, which comprises a control unit and an electrode device, which is adapted to be applied to the current-application site. The control unit drives the electrode device to apply a current to the site. Stimulation techniques may be used that are described in one or more of the applications incorporated hereinbelow by reference.

Such nervous tissue stimulation generally improves the engraftment of the progenitor or genetically-modified cells, improves survival of the cells, and enhances the function of the cells within the target tissue. For example, such parasympathetic stimulation may enhance the contractility and survival of progenitor cells implanted in the myocardium. Alternatively or additionally, such stimulation reduces inflammation.

For some applications, the patient suffers from a myocardial infarct or heart failure, while for other applications the patient suffers from neither a myocardial infarct nor heart failure. For some applications, the current is configured to control (e.g., pace) a heart rate of the patient, while for other applications, the current is not configured to control (e.g., pace) the heart rate.

For some applications, such cells are administered to facilitate cardiac repair. For these applications, nervous tissue stimulation generally enhances blood supply and/or angiogenesis.

In an embodiment of the present invention, a method for enhancing progenitor or genetically-modified cell therapy comprises administering progenitor or genetically-modified cells to a patient, and applying non-electrical stimulation to a site of the patient. Such non-electrical stimulation may include, for example, administration of a drug, such as a drug that blocks sympathetic activity (i.e., a sympatholytic drug), such as a beta blocker; a drug that increases vagal tone, such as directly-administered acetylcholine; a chronotropic drug; an adrenergic blocking drug; or an anti-inflammatory drug.

In some embodiments of the present invention, progenitor or genetically-modified cells are administered to promote:
the function of the heart;
the function of the liver;
the function of kidneys;
the function of bone marrow;
the function and growth of skin;
the function of the digestive system;
the function of the immune system;
the function of neural tissue;
the function of blood vessels;
the production of blood cells; and/or
the growth of hair.

In an embodiment of the present invention, a method for enhancing migration and/or differentiation of progenitor or genetically-modified cells comprises applying an electrical current to a site of a patient, without administering any cells to the patient, and configuring the current to enhance migration and differentiation of native progenitor or genetically-modified cells of the patient. For some applications, the current is configured to enhance migration and differentiation of the cells to promote the function of the heart, the function of the liver, the function of kidneys, the function of bone marrow, the function and growth of skin, the function of the digestive system, the function of the immune system, the function of neural tissue, the function of blood vessels, the production of blood cells, and/or the growth of hair.

In an embodiment of the present invention, progenitor or genetically-modified cells are administered directly (e.g., intravenously, by injection, or using a transdermal patch) to a systemic blood circulation of a patient. The cells are directed to a target treatment site, such as an organ, by applying a current to a current-application site remote from the target treatment site, or to a current-application site related to the target treatment site, and configuring the current to stimulate nervous tissue of the patient in a vicinity of the current-application site.

The following table shows examples of target treatment sites and associated current-application sites:

| Target treatment site | Current-application site(s) |
| --- | --- |
| The heart | A site containing parasympathetic tissue, such as the vagus nerve, an epicardial fat pad, a carotid artery, a coronary body, a coronary sinus, a vena cava vein, or an internal jugular vein |
| The liver | The vagus nerve or any of its branches |
| The brain | Peripheral nerves, cranial nerves, or the brain |
| Peripheral nerve(s) | Peripheral nerves, the spinal cord, or the brain; or The tissue that is innervated by the nerve (e.g. the muscle is the target site for a motor neuron nerve) |

In an embodiment of the present invention, administering the progenitor or genetically-modified cells comprises administering cells capable of differentiating into contractile units after administration, such as skeletal myoblasts or smooth muscle myoblasts. In an embodiment of the present invention, administering the progenitor cells or genetically-modified cells comprises administering cells capable of differentiating into endothelial cells after administration, such as bone marrow progenitor cells or genetically-modified cells.

In an embodiment of the present invention, applying the current comprises configuring the current to enhance capillary growth at a heart site of the patient. In an embodiment of the present invention, applying the current at current configuration step 104 comprises configuring the current to reduce arrhythmia that may be caused by administration of progenitor or genetically-modified cells. In an embodiment of the present invention, applying the current comprises configuring the current to reduce inflammation at a heart site of the patient, for example, to reduce complications/adverse events that might result from cell administration (such as calcifications or arteriogenesis).

In an embodiment of the present invention, configuring the current to enhance the measure of functionality of the cells comprises configuring the current to decrease a rate of mortality of the progenitor or genetically-modified cells.

In an embodiment of the present invention, applying the current comprises: placing a set of one or more electrodes within a body of the patient, applying the current while the set of electrodes is within the body, and removing the set of electrodes from the body within 8 weeks following placing the set of electrodes within the body, e.g., within 2 to 8 weeks.

Alternatively, applying the current comprises chronically implanting the electrodes in the body, e.g., leaving the electrodes in the body for more than 8 weeks. For some applications, the current is applied only within 8 weeks or within 48 hours of administering the cells. For some applications, current is applied for longer periods after administration of the cells, such as for several months after administration of the cells. For some applications in which the device is chronically implanted, current is applied only temporally adjacent to administering the progenitor or genetically-modified cells. Current is typically applied for at least one hour before the administration and/or for at least three hours following the administration.

For some applications, applying the current comprises applying the current after and not before administering the progenitor or genetically-modified cells. Alternatively, applying the current comprises initiating application of the current before administering the progenitor or genetically-modified cells, such as at least one day prior to administering the progenitor or genetically-modified cells.

For some applications, applying the current comprises applying the current before and after administering the progenitor or genetically-modified cells. Alternatively, for some applications, applying the current comprises applying the current before and not after administering the progenitor or genetically-modified cells.

In an embodiment of the present invention, applying the current comprises assessing a response of the patient to the application of the current, prior to administering the progenitor or genetically-modified cells, and modifying an administration parameter of the administration of the progenitor or genetically-modified cells in response to the assessment, such as a route of the administration, a cell type, or an amount (e.g. a number) of cells. For some applications, modifying the administration parameter comprises modifying an amount (e.g. a number) of the progenitor or genetically-modified cells administered in response to the assessment. For example, the number of cells may be increased whenever a change in a heart performance parameter is not considered satisfactory. Alternatively or additionally, modifying the administration parameter comprises modifying a time of administration of the progenitor or genetically-modified cells, in response to the assessment. Further alternatively or additionally, modifying the administration parameter comprises modifying a ratio of types of the progenitor or genetically-modified cells administered, in response to the assessment.

For some applications, the administration parameter is held constant while an improvement in a heart response of the patient is considered satisfactory. For some applications, a parameter of the applied current is modified whenever a change in a heart performance parameter is not considered satisfactory.

For some applications, assessing of the response comprises imaging the target organ (such as by CT, MRI, US, or Doppler), assessing blood flow to the target organ, or performing biochemical analysis of gene expression in the target organ.

For some applications, the current is applied using one or more of the following parameters:
  a current amplitude in the range of about 1 to about 20 mA (e.g., 3, 5, 10, or 15 mA);
  a current frequency in the range of about 0.01 to about 10 Hz (e.g., 0.05, 0.5, or 3 Hz);
  a pulse width in the range of about 0.1 to about 4 ms (e.g., 0.5, or 1.5 ms); and/or
  intermittent activation during "on" and "off" periods, each having durations of between about one second to about one day (e.g., one minute, or one hour).

For some applications, application of the current is synchronized with the cardiac cycle. For some applications, the current is applied during the refractory period of the heart. For some applications, the current is applied with an amplitude less than the pacing threshold, which is generally less than 2 mA. It is noted that the pacing threshold varies for each patient, and with the positioning of each electrode.

For some applications, current is applied directly to the liver, or to another organ of the patient. In this case, the cells are typically, but not necessarily, administered to the organ to which the current is applied.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 10/205,474, filed Jul. 24, 2002, entitled, "Electrode assembly for nerve control," which published as US Patent Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," which published as PCT Publication WO 03/01811 and U.S. patent application Ser. No. 10/488,334, filed Feb. 27, 2004, in the US National Phase thereof, now U.S. Pat. No. 7,734,355

U.S. patent application Ser. No. 09/944,913, filed Aug. 31, 2001, entitled, "Treatment of disorders by unidirectional nerve stimulation," now U.S. Pat. No. 6,684,105

U.S. patent application Ser. No. 10/461,696, filed Jun. 13, 2003, entitled, "Vagal stimulation for anti-embolic therapy," now U.S. Pat. No. 7,321,793

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions," now U.S. Pat. No. 7,778,711

A PCT patent application PCT/IL03/00440, filed May 23, 2004, entitled, "Selective nerve fiber stimulation for treating heart conditions," which published as PCT Publication WO 04/103455

U.S. patent application Ser. No. 10/866,601, filed Jun. 10, 2004, entitled, "Applications of vagal stimulation," which published as U.S. Patent Application Publication 2005/0065553

A PCT patent application PCT/IL04/00496, filed June 10, 2004, entitled, "Vagal stimulation for anti-embolic therapy," which published as PCT Publication WO 04/110550, and U.S. patent application Ser. No. 10/560,654 national stage thereof, now U.S. Pat. No. 7,8885,711

U.S. Provisional Patent Application 60/478,576, filed Jun. 13, 2003, entitled, "Applications of vagal stimulation"

U.S. patent application Ser. No. 11/280,884, filed Nov. 15, 2005, entitled, "Techniques for nerve stimulation," now U.S. Pat. No. 7,627,384

U.S. patent application Ser. No. 11/234,877, filed Sep. 22, 2005, entitled, "Selective nerve fiber stimulation," now U.S. Pat. No. 7,885,709

U.S. patent application Ser. No. 11/062,324, filed Feb. 18, 2005, entitled, "Techniques for applying, calibrating, and controlling nerve fiber stimulation," now U.S. Pat. No. 7,634,317

U.S. patent application Ser. No. 11/064,446, filed Feb. 22, 2005, entitled, "Techniques for applying, configuring, and coordinating nerve fiber stimulation," now U.S. Pat. No. 7,974,693

U.S. patent application Ser. No. 11/022,011, filed Dec. 22, 2004, entitled, "Construction of electrode assembly for nerve control," now U.S. Pat. No. 7,561,922

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising: selecting a patient suffering from a heart condition;
   selecting cells capable of promoting function of a heart of the patient, the cells selected from the group consisting of: bone marrow progenitor cells, genetically-modified bone marrow progenitor cells, and myoblasts;
   administering the cells to the patient; applying an electrical current to a site of the patient in a vicinity of parasympathetic nervous tissue, wherein applying the current comprises initiating application of the current before administering the cells, and applying the current only within 48 hours of a time of administering the cells; and configuring the current to stimulate the parasympathetic nervous tissue to reduce arrhythmia that may be caused by administration of the cells, wherein cardiac repair is facilitated, blood supply is enhanced and/or angiogenesis is enhanced.

2. The method according to claim 1, wherein applying the current comprises applying the current to an epicardial fat pad.

3. The method according to claim 1, wherein applying the current comprises synchronizing application of the current with a cardiac cycle of the patient.

4. The method according to claim 3, wherein applying the current comprises applying the current during a refractory period of heart of the patient.

5. The method according to claim 1, wherein applying the current comprises applying the current with an amplitude less than a pacing threshold of the heart.

6. The method according to claim 1, wherein the cells are selected from the group consisting of: skeletal myoblasts, and smooth muscle myoblasts, and wherein administering the cells comprises administering the selected myoblasts.

7. The method according to claim 1, wherein the site is selected from the group consisting of: a carotid artery, a coronary body, a coronary sinus, a vena cava vein, and an internal jugular vein, and wherein applying the current to the site comprises applying the current to the selected site.

8. The method according to claim 1, wherein the site includes a portion of a vagus nerve that innervates the heart, and wherein applying the current comprises applying the current to the portion of the vagus nerve that innervates the heart.

9. The method according to claim 1, wherein configuring the current to stimulate the parasympathetic nervous tissue comprises setting the current to have an amplitude between 1 and 20 mA, and a frequency between 0.01 and 10 Hz.

10. A method comprising: selecting a patient suffering from a heart condition;
    selecting cells capable of promoting function of a heart of the patient, the cells selected from the group consisting of: bone marrow progenitor cells, genetically-modified bone marrow progenitor cells, and myoblasts; administering the cells to the patient; applying an electrical current to a site of the patient in a vicinity of parasympathetic nervous tissue, wherein applying the current comprises initiating application of the current before administering the cells, and assessing, prior to administering the cells, a response of the patient to the application of the current, and modifying an administration parameter of the administration of the cells in response to the assessment; and configuring the current to stimulate the parasympathetic nervous tissue to reduce arrhythmia that may be caused by administration of the cells,
    wherein cardiac repair is facilitated, blood supply is enhanced and/or angiogenesis is enhanced.

11. The method according to claim 10, wherein applying the current comprises applying the current to an epicardial fat pad.

12. The method according to claim 10, wherein applying the current comprises synchronizing application of the current with a cardiac cycle of the patient.

13. The method according to claim 12, wherein applying the current comprises applying the current during a refractory period of heart of the patient.

14. The method according to claim 10, wherein applying the current comprises applying the current with an amplitude less than a pacing threshold of the heart.

15. The method according to claim 10, wherein the cells are selected from the group consisting of: skeletal myoblasts, and smooth muscle myoblasts, and wherein administering the cells comprises administering the selected myoblasts.

16. The method according to claim 10, wherein the site is selected from the group consisting of: a carotid artery, a coronary body, a coronary sinus, a vena cava vein, and an internal jugular vein, and wherein applying the current to the site comprises applying the current to the selected site.

17. The method according to claim 10, wherein the site includes a portion of a vagus nerve that innervates the heart, and wherein applying the current comprises applying the current to the portion of the vagus nerve that innervates the heart.

18. The method according to claim 10, wherein configuring the current to stimulate the parasympathetic nervous tissue comprises setting the current to have an amplitude between 1 and 20 mA, and a frequency between 0.01 and 10 Hz.

* * * * *